United States Patent [19]

Van den Berg et al.

[11] Plant 4,727

[45] May 26, 1981

[54] KALANCHOE PLANT

[75] Inventors: Cornelis P. Van den Berg; James C. Mikkelsen, both of Ashtabula, Ohio

[73] Assignee: Mikkelsens Inc., Ashtabula, Ohio

[21] Appl. No.: 134,116

[22] Filed: Mar. 26, 1980

[51] Int. Cl.[3] ..... A01H 5/00

[52] U.S. Cl. ..... Plt./68

[58] Field of Search ..... Plt./68

*Primary Examiner*—James R. Feyrer

*Attorney, Agent, or Firm*—Schwartz, Jeffery, Schwaab, Mack, Blumenthal & Koch

[57] ABSTRACT

A kalanchoe plant, known by the cultivar name Sensation, and particularly characterized by its excellent keeping quality, free branching habit, well clustered, red-purple flowers, highly floriferous and vigorous habit, and adaptability to various pot sizes and to growth regulators.

1 Drawing Figure

The present invention relates to a new and distinctive variety of kalanchoe plant, botanically known as *Kalanchoe blossfeldiana Poelln,* and referred to by the cultivar name Sensation. The cultivar was developed by us through controlled breeding by crossing Solferinopurpur (seed parent) and Feuerball (pollen parent). Solferinopurpur is disclosed in U.S. Plant Pat. No. 3,843 and the pollen parent Feuerball is disclosed in U.S. Plant Pat. No. 3,861. Asexual reproduction by stem cuttings has shown that the unique features of Sensation are stabilized and are reproduced true to type in successive propagations.

The following characteristics distinguish Sensation from both its parent varieties and other cultivated kalanchoes of this type known and used in the floriculture industry:

1. Sensation was selected especially for the excellent keeping quality of the foliage and the flowers, both in the greenhouse and in the home, which is far superior to that of either parent.
2. Freely branching, with or without pinching, comparable to that of Feuerball and better than that of Solferinopurpur.
3. Plant growth is more vigorous than that of either parent.
4. Proper scheduling makes new cultivar suitable for production in 10 to 15 cm. pots.
5. After flower initiation, the growth of the terminal shoot slows down, resulting in approximately the same length of the terminal and side peduncles at flowering time, adding to the total flower placement.
6. After flower initiation, plants must be treated with B9 in all seasons to reduce peduncle elongation.
7. Flowering time is 10 weeks in summer to 14 weeks in winter after start of short days.
8. Well clustered red-purple flowers, and highly floriferous.
9. Flowers are approximately the same size as those of Solferinopurpur, and larger than those of Feuerball.
10. Leaves are larger than those of either parent and have a dark green shiny appearance.

The accompanying colored photograph illustrates the overall appearance of Sensation. The photograph is a top perspective view of the plant and shows the colors as true as it is reasonably possible to obtain in a colored reproduction of this type.

The following is a detailed description of our new kalanchoe variety based on plants produced under commercial practices in the greenhouses of Mikkelsens Inc., Ashtabula, Ohio.

Parentage:

A controlled cross of the cultivar Solferinopurpur as the seed parent and the cultivar Feuerball as the pollen parent.

Propagation:

(A) *Type cutting.*—Short tip cutting, with stems up to 2 cm. long.

(B) *Time to root.*—10 days at 21° C. summer, 14 days at 21° C. winter.

(C) *Rooting habit.*—Many very fine roots, fibrous.

Plant description:

(A) *Form.*—Short, compact, upright growth. Growing and scheduling practices can produce a small plant in a 10 cm. pot up to a larger plant in a 15 cm. pot.

(B) *Habit of growth.*—Rate of growth moderate for this type of plant. Generally, shoots are formed at every node.

(C) *Foliage description.*—Leaves simple, opposite. Frequently, leaves are asymmetrical, with a slight tendency to bend or twist. (1) Size: Average full grown leaf 130 mm. long × 80 mm. wide. Full grown leaves have petioles up to 30 mm. long; young leaves have short petioles. (2) Shape: Ovate to elliptic, apex obtuse, base attenuate. (3) Texture: Glabrous, coriaceous, succulent. (4) Margin: Sinuate to crenate. (5) Color: Young foliage, top side green 137B, under side green 138A. Mature foliage, top side darker than green 137A to yellow green 147A, under side green 137A-B.

Flowering description:

(A) *Flowering habits.*—Inflorescence of each shoot is formed by dichotomous branching, starting with opening of terminal flower of main axis, followed by terminal flowers of the side branches, continuing with subsequent development of branches in the inflorescence. Opening of new buds will continue for two months or more. Individual flowers last two weeks or more after opening.

(B) *Natural flowering season.*—Late January. Flowering time under controlled daylength at 20° C. in summer is 10 weeks; in winter 14 weeks.

Flowering time depends on temperature, light intensity and other growing conditions.

(C) *Flower bud description.*—Elliptical to oblong, up to 8 mm. long, developing to tubular as flower petals mature, sheathed with four green sepals. Corolla at maturity, 8 mm. long.

(D) *Flowers borne.*—Compound dichasial cyme on strong peduncles. Primary peduncle is 5 mm. in diameter, with peduncle length depending on growing conditions and B9 application; pedicels up to 8 mm. long.

(E) *Quantity of flowers.*—Highly floriferous. Main axis and side shoots have 100 or more flowers.

(F) *Petals.*—(1) Shape: Nearly round, with top slightly cuspidate. (2) Color: Top side when opening red-purple 57B, fading to red-purple 58C, under side, red purple 63D, infused with green. (3) Number of petals: Four (4), united in corolla, salverform; petals 6 mm. in diameter, and total flower diameter 16 mm.

(G) *Reproductive organs.*—(1) Stamens: Eight (8) in number, (a) Anther shape: flat, elliptical, color light brown; frequently, anthers are degenerated, with dark brown color. (b) Filament color: light green. (c) Pollen color: yellow. (2) Pistils: (a) Stigma shape: flat, crystalline, color greenish white. (b) Style color: light green. (c) Ovary: 4 celled, 6 mm. long, color green 143A.

Disease resistance;

No diseases or adverse physiological problems observed to date. Cultivar is highly resistant to mildew.

We claim:

1. A new and distinct cultivar of kalanchoe plant, known by the cultivar name Sensation, as described and illustrated, and particularly characterized by its excellent keeping quality, free branching habit, well clustered, red-purple flowers, highly floriferous and vigorous habit, and adaptability to various pot sizes and to growth regulators.

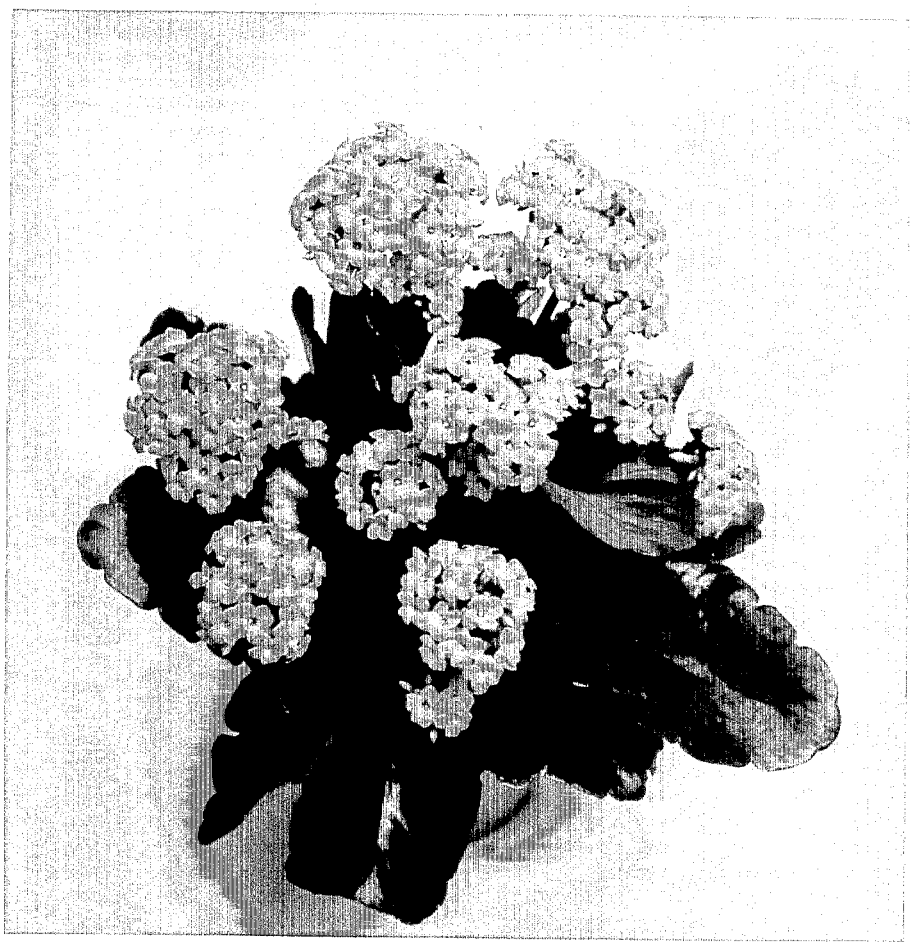

* * * * *